(12) United States Patent
Schapmire

(10) Patent No.: US 6,216,535 B1
(45) Date of Patent: Apr. 17, 2001

(54) APPARATUS FOR TESTING ISOINERTIAL LIFTING CAPACITY

(75) Inventor: Darrell William Schapmire, 128 Madison St., Hopedale, IL (US) 61747

(73) Assignee: Darrell William Schapmire

( * ) Notice: Subject to any disclaimer, the term of this patent is extended or adjusted under 35 U.S.C. 154(b) by 0 days.

(21) Appl. No.: 09/361,200

(22) Filed: Jul. 26, 1999

(51) Int. Cl.⁷ .............................. A61B 5/22; G01N 19/00
(52) U.S. Cl. ...................................... 73/379.08; 73/865.9
(58) Field of Search ................... 73/379.01, 379.02, 73/379.03, 379.08, 865.9

(56) References Cited

U.S. PATENT DOCUMENTS

| | | | |
|---|---|---|---|
| 3,465,592 | 9/1969 | Perrine | 73/379 |
| 3,982,757 | * 9/1976 | McDonnell | 482/123 |
| 4,337,050 | 6/1982 | Engalitcheff, Jr. | 434/260.62 |
| 4,423,862 | * 1/1984 | Hewitt | 482/130 |
| 4,451,037 | * 5/1984 | O'Hare | 473/445 |
| 4,473,226 | 9/1984 | Siegel et al. | 272/132 |
| 4,475,408 | 10/1984 | Browning | 73/862.12 |
| 4,907,797 | 3/1990 | Gezari et al. | 272/129 |
| 4,972,711 | 11/1990 | Jain et al. | 272/129 |
| 5,151,071 | 9/1992 | Jain et al. | 482/101 |
| 5,275,045 | 1/1994 | Johnston et al. | 73/379.01 |
| 5,435,799 | * 7/1995 | Lundin | 482/8 |

* cited by examiner

Primary Examiner—Max Noori

(57) ABSTRACT

A lever arm for testing consistency of effort during a lifting assessment has a plurality of measurement points at intervals along the length of the device. The lever arm pivots on a fulcrum located at the distal end of the device. The fulcrum consists of a rod which is supported in a horizontal position by a plurality of bearing boxes affixed to the distal end of the lever arm and a plurality of bearing boxes affixed to a base which is secured to, or rests on, a surface. This arrangement allows the lever arm to pivot in an arc when the proximal end of the device is lifted by the test subject. Workloads are applied to the lever arm and secured at said measurement points with a weight retaining assembly. Said weight retaining assembly contains a roller bar to which a plurality of barbell weighs can be affixed. At the clinician's option, simultaneous use of more than one weight retaining assembly can be employed during a test protocol as a "distraction testing" technique in assessing validity of effort. A clinician regulates the height of a subject-held handle plate by means of an adjustable chain linking system, adjusting the length of said linking system to the anthropomorphic requirements of the subject. The adjustable chain linking system connects said handle plate with the proximal end of the invention and the center of said handle plate. Using a system that includes 60 barbells of various weights and two weight retaining apparatuses, more than 1.5 million combinations of workloads are mathematically possible in a two trial protocol. Thus, using a multiple trial protocol, it is possible to assess consistency of effort during a functional test for lifting capacity. The amount of weight lifted by a subject can be determined by referring to a table provided with the equipment.

1 Claim, 8 Drawing Sheets

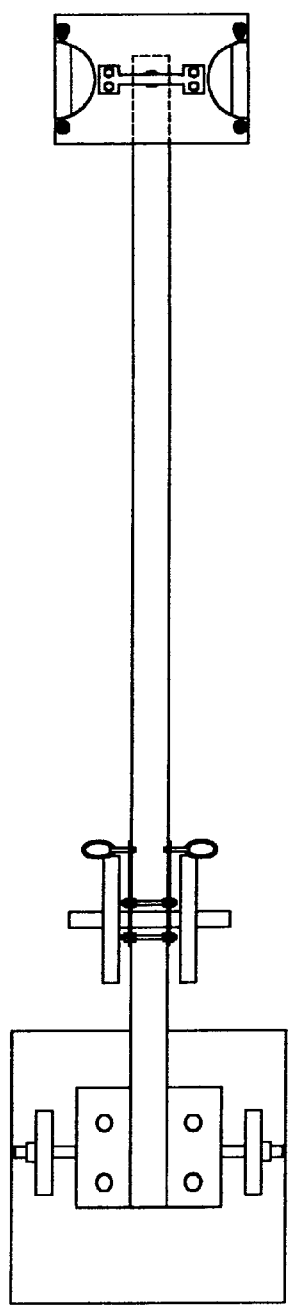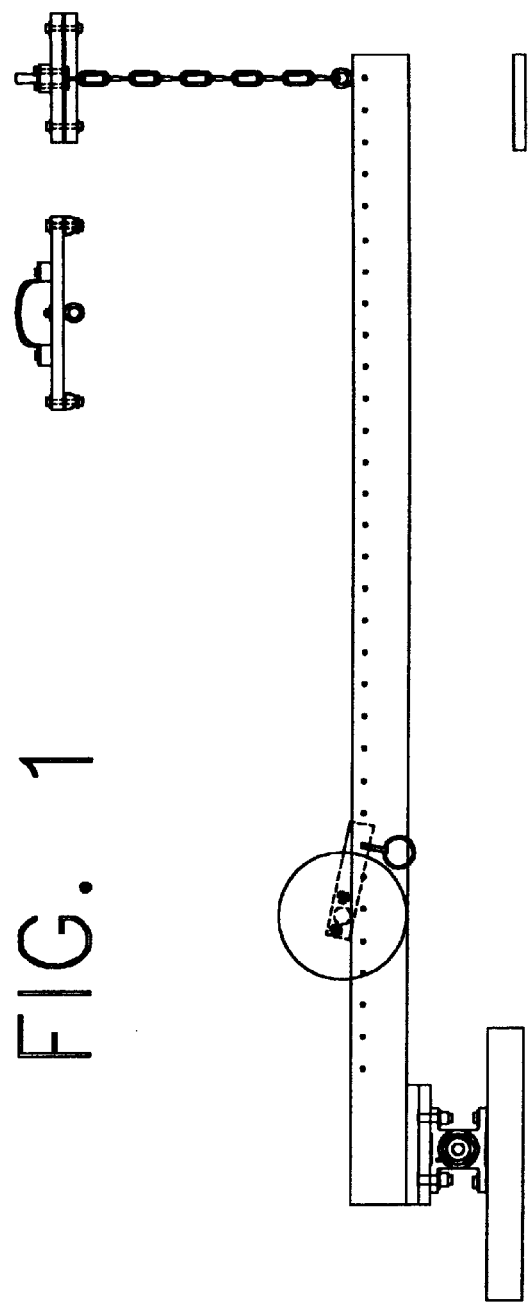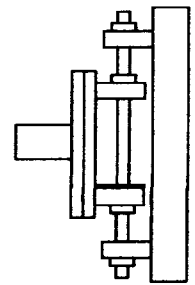
FIG. 1

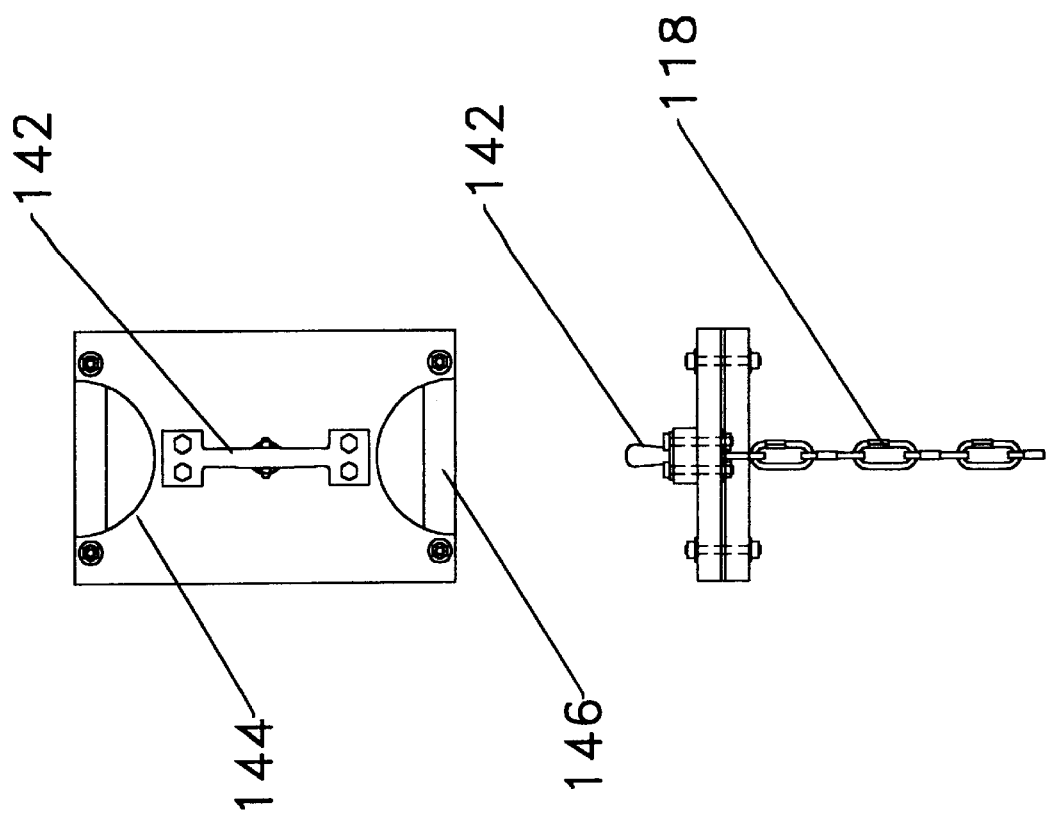
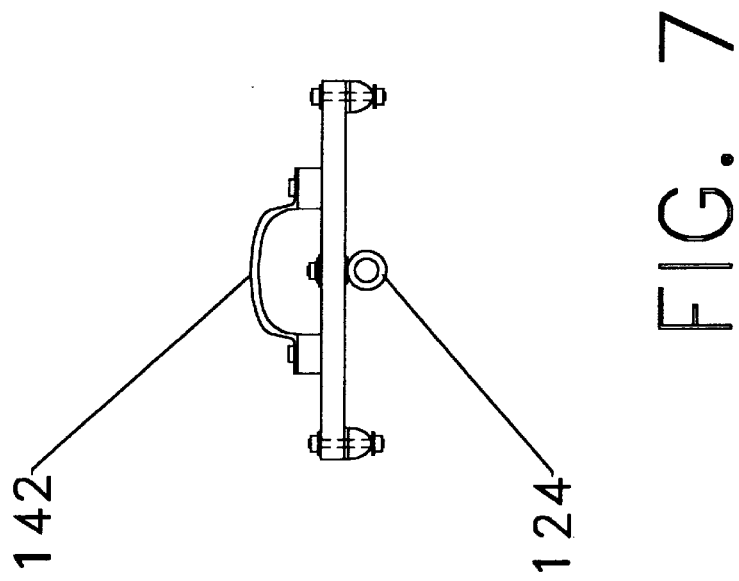
FIG. 7

APPARATUS FOR TESTING ISOINERTIAL LIFTING CAPACITY

1. Field of Invention

This invention relates to isoinertial lifting capacity testing devices, specifically such non-computerized equipment which is used to assess consistency of effort during a functional capacity evaluation. Various equipment and methodologies are currently in use to evaluate validity of effort in subjects who have filed insurance claims for physical injury.

2. Description of Prior Art

Work-related injuries represent a major source of financial loss for businesses in this country. Significant claims for personal injury also arise from motor vehicle accidents and other accidents which are unrelated to the workplace. Together, the medical and indemnity expenses associated with these claims cost billions of dollars annually.

A disproportionate amount of money in compensable cases is spent on a relatively small number of claims which are filed. In part, this occurs because some claimants may need to undergo surgery and/or extensive physical rehabilitation. In other cases, expenses related to treatment, rehabilitation and indemnity are inflated because individuals may attempt to abuse a compensation system and receive treatment or monetary awards that are not justified.

Various physical tests are often performed to determine the need for treatment, to make appropriate return to work restrictions or to arrive at a financial settlement for a case. In such tests it is essential that measures be incorporated in a protocol to objectively identify performances that are not reflective of maximum efforts.

Not infrequently during an assessment of an individual's functional abilities, apparent inconsistencies in performance are noted. The classic example of such inconsistent behaviors may occur during a hand grip assessment in which a low back pain patient demonstrates physical weakness and wide variability between trials on a hand-held dynamometer. (Hand grip weakness can not be explained in the physical context of a low back injury.) Some individuals in a testing or therapeutic environment, then, appear to magnify the extent of pain and disability because of non-physical factors. Mechanic and Matheson have written extensively about this phenomenon, known in the field as "symptom magnification."

In some cases, unrealistic expectations are placed upon injured workers who are attempting to return to work after an injury. Without objective information regarding an individual's functional abilities, employers and insurance companies may expose a worker to re-injury. Furthermore, financial settlements proposed in such instances may not adequately compensate an injured party.

As a result of abuses of compensation systems by claimants and defendants alike, there is a demand for comprehensive functional assessment. Such evaluations can be used to assess validity of effort and to manage decisions regarding indemnity, treatment and an individual's ability to return to work.

In compensation systems, thus, it is necessary to objectively determine if a physical performance reflects maximum physical effort. Performances that are not highly reproducible can not logically be classified as valid expressions of maximum physical capacity. Therefore, it has become beneficial to develop tools and methods which help clinicians objectively assess consistency of effort during a test of functional abilities, particularly during lifting, carrying, pushing and pulling, because these are the most commonly performed material handling tasks.

Susan Isernhagen proposes the "kinesiophysical" approach to functional assessment. A standard protocol is administered to test subjects. Using this method of evaluation, therapists are reportedly able to identify valid efforts by noting the presence or absence of biomechanical failure during assessments of lifting, carrying, pushing and pulling capacities. Isernhagen proposes specific criteria which are said to indicate biomechanical breakdown and valid effort. The application of the criteria, however, relies on the accuracy of the therapist's assessment of the physical performance, as opposed to extensive analysis of numerical data gathered during the test.

In the kinesiophysical model, termination points for various material handling tasks in this protocol are determined by the therapist. Inter-tester variability in interpretation of performance is inevitable with such an approach. A subjective approach has the potential to expose a test subject to injury if a therapist misjudges physical ability or effort. There is also the potential to incorrectly classify consistency of effort. The evaluation of symptom magnification does not play an important role in the approach advocated by Isernhagen.

Matheson and Blankenship propose the "psychophysical" method of functional assessment. These clinicians propose that any physical performance is affected by psychological as well as physical factors. The psychophysical approach is the most common type of protocol used to evaluate claimants in a compensation system.

Material handling activities during a psychophysical assessment are terminated when a test subject indicates an inability to safely perform at a higher workload or when, in the clinician's opinion, the safe biomechanical limits of the subject have been attained. Both of these termination points are subjective. In contradistinction to the kinesiophysical approach, the method advocated by Matheson and Blankenship places more emphasis on interpretation of raw data in order to add some objectivity to the assessment of validity of effort. Furthermore, Matheson and Blankenship place a greater value on incorporating cross-reference tests and observations into a protocol. Psychological and behavioral factors are also given more weight in the analysis of a performance. For example, Waddell testing for assessing non-physical pain responses in low back pain patients are routinely administered. (In landmark research, Gordon Waddell found a correlation between reports of pain arising from purposely-benign physical maneuvers and high scores for hypochondriasis, hysteria and depression on the Minnesota Multiphasic Personality Inventory.) Pain questionnaires intended to identify possible symptom magnification are also typically filled out by the subjects in the psychophysical model.

Matheson and Blankenship also advocate the use of various multiple-trial isometric tests to assess consistency of effort. Inter-test variability between trials is analyzed with the coefficient of variation. It is noted, though, that the research on the coefficient of variation is divided as to the usefulness of this statistic in correctly classifying effort during isometric strength testing.

"Distraction testing" has become an accepted method of assessing consistency of effort. Waddell formally proposed the concept in the research previously cited. He insisted that for such testing to be valid, it must be "non-emotional, non-hurtful and non-surprising." Clinicians using the psychophysical method of evaluation frequently develop their own distraction tests for use during functional assessment, varying the protocols proposed by Matheson and Blankenship in accordance with their professional experience and judgement.

There are a variety of testing devices capable of measuring isometric lifting capacities. Examples of a few such inventions include U.S. Pat. Nos. 4,972,711 and 5,275,045. This mode of testing maintains the test subject in a static body posture while the subject exerts a pushing, pulling or lifting force against a stationary object. However, there are few work-related activities which require the production of force which is exerted against an immovable object. Also, there is no direct relationship between isometric and dynamic physical abilities. Furthermore, clinical research, as already stated, is divided on the usefulness of the coefficient of variation in assessing consistency of effort during isometric tasks.

Numerous isokinetic devices have been invented. Examples of such inventions are U.S. Pat. Nos. 3,465,592 and 4,907,797. Some isokinetic devices have the capability to measure lifting abilities while others test or exercise isolated joints and groups of muscles. All of these devices apply an accommodating resistance to the test subject's efforts. Through mechanical and/or electronic means, the workload is adjusted continuously during a test to match the force being applied by the user, thereby allowing for movement at a constant velocity. This artificial workload is significantly unlike the isoinertial workloads found in the workplace. Thus, there is no direct relationship between isokinetic physical capacities and the physical demands in the actual work environment. Furthermore, no standardized approaches to assessing consistency of effort for performances on this type of equipment has been developed. Instead, clinicians administering such tests usually assess consistency of effort by visual analysis of graphs which depict a performance. The variability between repetitions depicted in a graph are said to reflect differences between repetitions. However, the apparent differences between repetitions is, to a large degree, affected by the scale on which the axes of the graph are displayed. Thus, visual analysis of graphs is intuitive and results in inter-tester variability in interpretation.

U.S. Pat. No. 5,275,045 to Johnston electronically weighs workloads and records changes in various physical parameters during various isoinertial lifting and carrying tasks. A sophisticated electronic data collection system provides a descriptive account of a performance in terms of range of motion changes, velocities and acceleration for isoinertial activities. However, the invention provides no standardized or analysis with regard to validity of effort. The device is no longer in production by the manufacturer. A similar invention is described in U.S. Pat. No. 5,151,071. Neither of these devices are capable of measuring unilateral isoinertial lifting capacity.

Three inventions, U.S Pat. Nos. 4,337,959 and 4,473,226 and 4,475,408 are incorporated into a single piece of equipment, now commercially known as the "BTE Work Simulator." This device is commonly found in clinics throughout the country. It has a number of uses, including one feature which measures isoinertial lifting capacity. Workloads which are unseen are controlled by the clinician. The resistance is generated by an electromagnet which applies a workload to a pulley A rope is wound round the pulley and connected to a bar which is held by the test subject. The test subject exerts lifting force against the hand-held bar, pulling the bar and the rope through a range of motion. The workload applied by this equipment is isoinertial, the same type of resistance that would be encountered in the workplace. The Work Simulator, however, is capable of applying resistance in one direction only. Therefore, although the capacity of an individual to exert a lifting force can be assessed, the device is incapable of applying a workload when the subject returns the workload to its starting position. This is a significant disadvantage in a population of test subjects with orthopedic pathology because the ability to lift an object does not necessarily imply to the ability to safely lower the object to its resting position.

Basic testing equipment, such as dumbbells, usually have markings which indicate their weight. Such equipment, therefore, make objective assessment very difficult. Even workloads which are unmarked can provide sufficient visual information to allow some test subjects to estimate the amount of weight being lifted and thereby control the outcome of the assessment and, therefore, affect the objectivity of the test results.

Thus, there are several devices on the market which are used to assess isometric, isokinetic and isoinertial lifting capacities in the clinical setting. The present invention uses unmarked weights which can be secured at various measurement points on a lever arm to measure isoinertial lifting capacity. At the clinician's discretion, a single weight retaining assembly or a plurality of weight retaining assemblies can be placed at a plurality of measurement points. Sixty barbell weights are included in the system. Mathematically, more than 1.5 million possible workloads are possible in a two trial protocol using the device, thereby reducing the possibility for a subject to visually inspect and subsequently estimate a workload. Using a psychophysical approach to testing, a multiple trial protocol will facilitate objective assessment of consistency of effort. The isoinertial resistance is the same as that which is most often found in the "real world," making the test results relevant to lifting tasks performed on the job. All lifting assessment devices and protocols heretofore known suffer from a number of disadvantages:

a) Protocols relying on a therapist's visual observation of a subject to assess validity of effort depend on the accuracy of the subjective interpretation of performance and, thus, are prone to possible excessive inter-tester variability in interpreting test results. Testing protocols of this kind are vulnerable to legal challenge. Furthermore, if a test subject's abilities are misjudged by the therapist, injury or misclassification of effort can result.

b) Isometric devices measure a subject's capacity to generate lifting forces against an immovable object. Isometric capacity is not directly related to the ability to perform isoinertial tasks, such as are most often found in the workplace.

c) There is no clear consensus on the usefulness of the coefficient of variation in analyzing consistency of effort during isometric testing.

d) The isokinetic devices provide a descriptive account of the ability of a subject to lift an artificial workload that can be created only by devices in a clinical setting. However, there is no means by which an isokinetic performance can be used to predict the ability to lift the isoinertial workloads encountered in everyday life. Furthermore, with such equipment, there is no standardized method of assessing validity of effort.

e) The objectivity of a lifting assessment can be affected if workloads are labeled and the subject is aware of the amount of weight being lifted. Even unmarked workloads may be accurately estimated by some test subjects who are attempting to limit physical performance.

f) U.S. Pat. Nos. 5,151,071 and 5,275,045 provide extensive descriptive accounts of a subject's physical performance. Information regarding weight lifted and changes in velocity, acceleration and range of motion are accurately summarized in a computer-generated report. These devices also generate graphs depicting the changes in ranges of motion, velocity and acceleration during a performance. None of this information, however, adequately answers questions related to consistency of effort during a test of lifting abilities. U.S. Pat. No. 5,151,071 uses weights which can be estimated by visual inspection. Additionally, the weighing feature, while computerized and quite accurate, merely restates what the clinician can easily calculate inasmuch as the weights used for this system are 5 pound and 10 pound bags of metal shot. Thus, the weight can be mentally calculated when the bags are added to the mechanical arm of the device, making the use of a computer or scales unnecessary.

g) U.S. Pat. Nos. 5,151,071 and 5,275,045 have no provision for measuring unilateral lifting capacities.

h) The BTE Work Simulator, protected by U.S. Pat. Nos. 4,337,050 and 4,473,226 and 4,475,408, provides accurate information regarding a an isoinertial workload that can not be visually inspected by the test subject. However, the invention provides resistance in one direction only. There is no means by which the equipment can be used to assess the ability of a test subject to return a workload to the starting position. This is a significant disadvantage, particularly in a patient population with true pathology.

i) Computerized equipment is costly to purchase and may require a substantial amount of training for a clinician to become proficient in its use. As a result, such equipment is difficult to cost-justify, particularly in light of the emphasis placed on cost containment in the field of health care.

OBJECTS AND ADVANTAGES

The purpose of this invention is to provide a device and protocol to objectively assess bilateral and unilateral lifting capacity. Specifically, the device is intended to provide objective information in evaluating consistency of effort between multiple trials of each activity. This goal is facilitated by using unmarked weights combined with the ability to apply a plurality of workloads at a plurality of measurement points along the length of the lever arm. This technique meets Gordon Waddell's criteria for "distraction testing" as cited previously.

Accordingly, several objects and advantages of the present invention are:

a) to reduce the reliance on the subjective assessment of a clinician regarding the consistency of effort of a subject during an isoinertial lifting assessment, replacing such assessment with a device which can be used in a multiple trial protocol to objectively evaluate consistency of effort during a lifting task.

b) to provide a device which tests a subject's lifting capacities in an isoinertial mode, such as is encountered in everyday life.

c) to provide a device which can be used to assess bilateral as well as unilateral lifting capacities.

d) to provide a device which allows for the assessment of the ability to lift weight as well as return the weight to the starting position.

e) to provide a device which is less costly and requires less training to become proficient in its use than computerized equipment.

f) to provide a device that needs no periodic re-calibration. Any given workload at any given measurement point on the lever arm will always offer the same resistance because of basic and unchanging laws of physics.

g) to provide a device which has few moving parts and will be inexpensive to maintain.

h) to provide a device which takes up a minimal amount of space and can be easily stored.

Further objects and advantages are to provide a device which is compact in size and easy to maintain. Because of the high number of mathematical permutations with regard to possible workloads on the invention, it will be possible to test the same subject multiple times during the course of rehabilitation. Therefore, familiarity with the testing device will not interfere with the objective measurement of consistency of effort.

It may be possible to assess body mechanics by observing the position of the handle plate and adjustable chain linking system relative to the lever arm. Often, such assessment is difficult when test subjects wear heavy or loose-fitting clothing. By observing not only the subject but also various structures on the device, the identification of biomechanical failure may be facilitated. For example, if the handle plate is not maintained in a level position during a lift, excessive lateral displacement of the spine or unequal distribution of the weight between the upper extremities could be indicated. If the adjustable chain linking system is not maintained in a vertical position during a lift, it is possible that the subject is failing to maintain a lordotic curve in the lumbar spine. Other objects and advantages will become apparent from a consideration of the ensuing description and drawings.

DRAWINGS

The following is a summary of the drawings of the present invention:

FIG. 1 depicts side and top views of the solid lever arm with the details which are depicted in the top view positioned immediately above corresponding details shown in the side view. End views of the solid lever arm and the handle plate are also shown.

FIG. 7 illustrates side, end and top views of the handle plate assembly used for the solid lever arm as well as the modified I-beam lever arm ramifications of the present invention.

Figure 8:
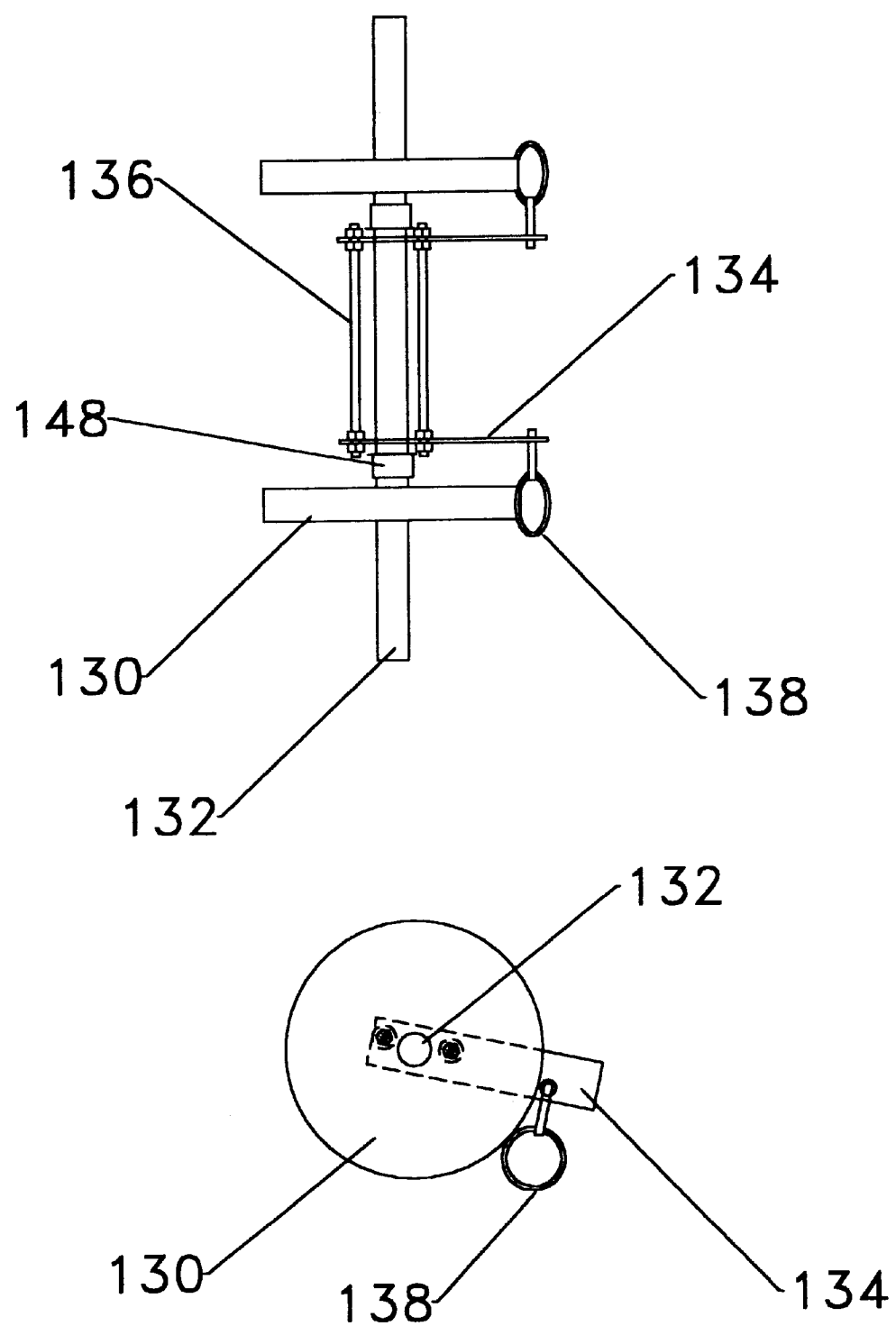

FIG. 8 depicts isolated side and top views of the weight retaining assembly and roller bar with barbell weights affixed to roller arm. Weight retaining assemblies of identical design as used in both ramifications of the present invention. However, dimensions of the weight retaining assembly are modified for each version to allow the assembly to rest across the width of each lever arm.

STRUCTURE

Figure 2:
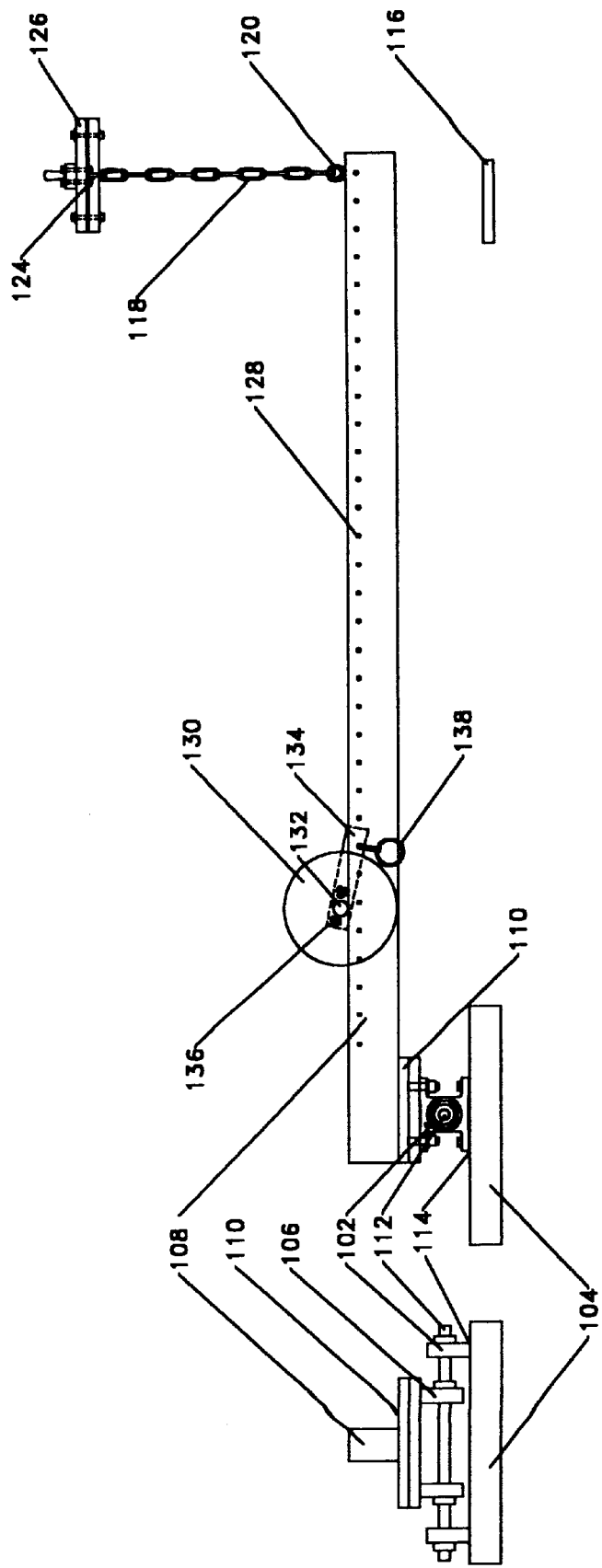
FIG. 2 shows the side and end views of the solid lever arm version of the present invention with the weight retaining assembly and barbell weights resting on the lever arm. The handle plate assembly and adjustable chain linking system which attaches said assembly to the lever arm are shown at the proximal end of the device.
Figure 3:
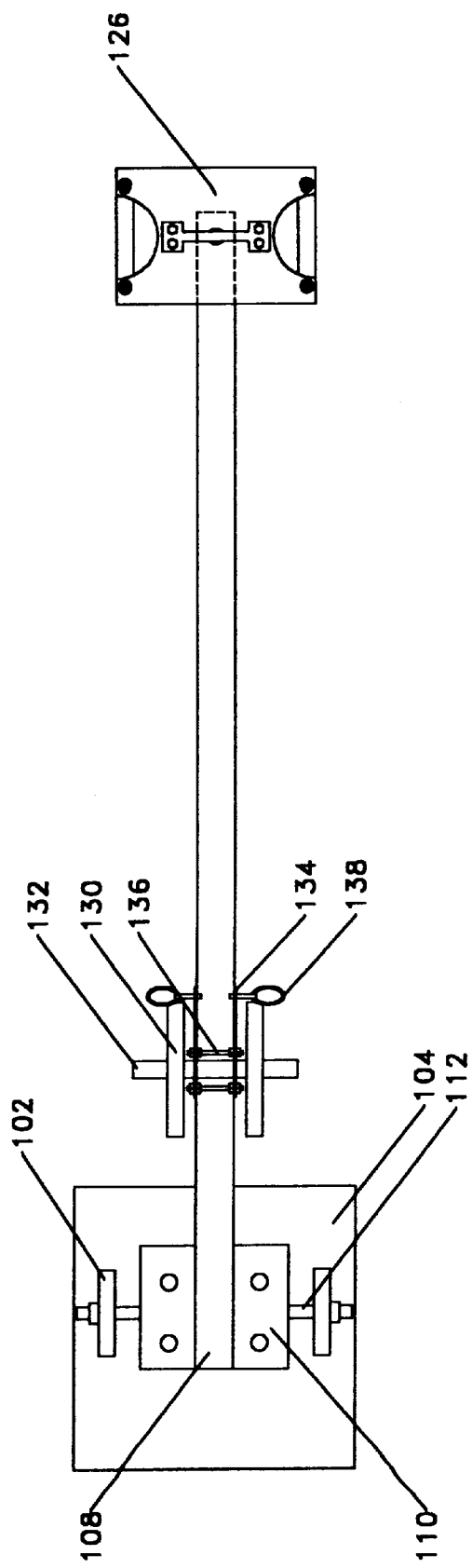
FIG. 3 shows the top view of the solid lever arm ramification of the present invention with the weight retaining assembly and barbell weights resting on the lever arm.
Figure 4:
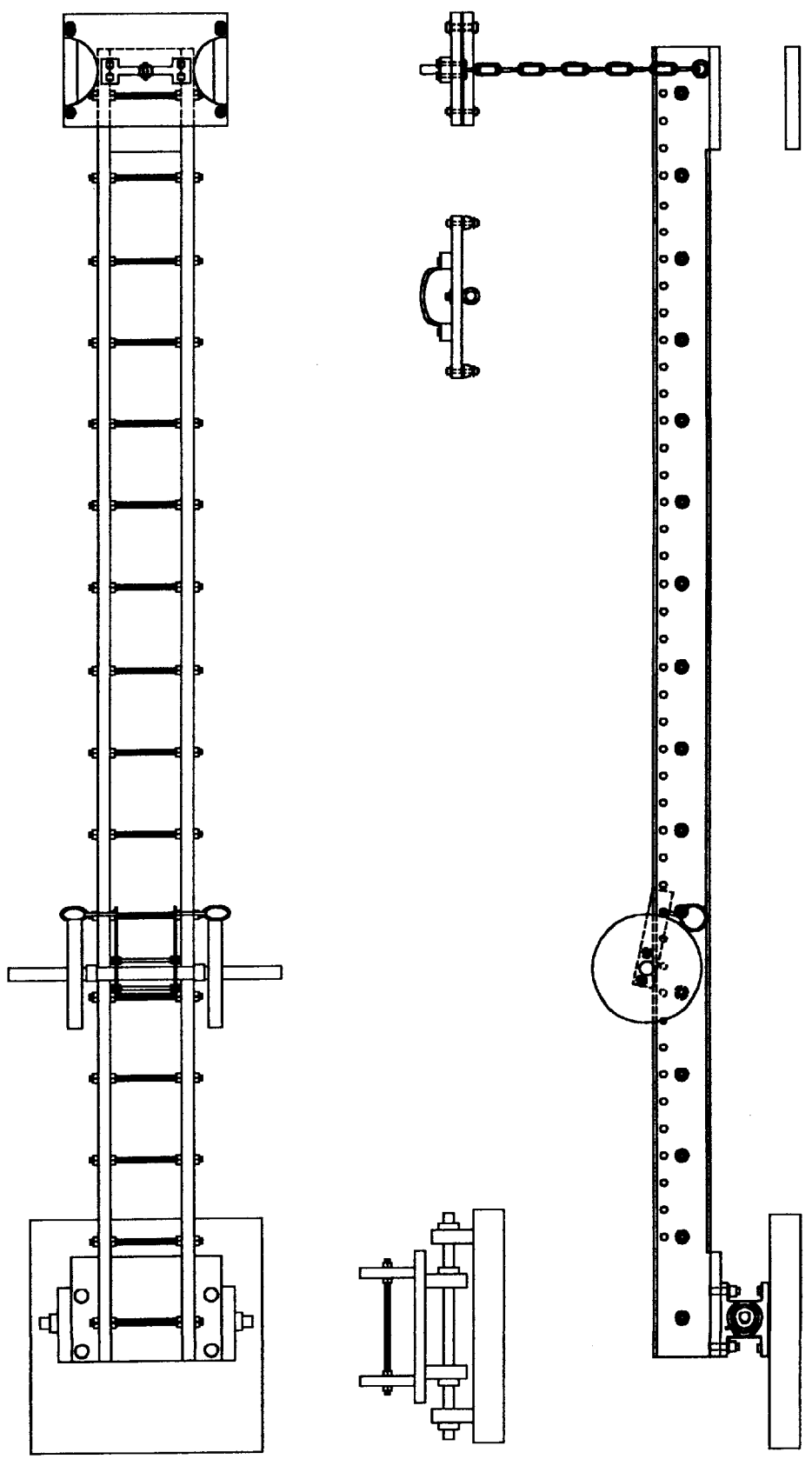
FIG. 4 depicts side and top views of the modified I-beam ramification with the details which are depicted in the top view positioned immediately above the corresponding details shown in the side view. End views of the modified I-beam and the handle plate are also shown.

Referring to FIG. 2 and FIG. 3 which depict a solid lever arm construction, primary bearing boxes 102 are mounted to a base 104. Secondary bearing boxes 106 are affixed to the distal end of a lever arm 108 on a foot plate 110. Said primary and secondary bearing boxes support a rod 112 in a horizontal position. Shims 114 are placed between said bearing boxes and said base to provide clearance between the base and the secondary bearing boxes. This arrangement allows said lever arm to pivot in an arc on said rod. The lever arm rests on a floor plate 116 prior to any lifting activity and serves to protect the floor from damage.

One end of an adjustable chain linking system 118 is attached to an eye hook 120 affixed to the proximal end of the lever arm. The other end of said adjustable chain linking system is attached to an eye hook 124 in the center of the bottom of a handle plate 126. (The handle plate and adjustable chain linking system are shown in detail in FIG. 7.) The adjustable chain linking system allows the height of said handle plate to be adjusted to the anthropomorphic requirements of the test subject. The use of said eye hooks and adjustable links allows for yawing, pitching and rolling movements of the handle plate to occur during a lift, as might occur during any isoinertial lifting activity in the "real world." In the drawing, the adjustable chain linking system is taut between the proximal end of the lever arm and said handle plate, as would occur during a lifting activity when the device is in use. Holes 128 in the lever arm are measurement points at which the weight retaining assembly and barbell weights 130 can be secured. Said weight retaining assembly comprises a roller bar 132, straps 134, stiffeners 136, and lynch pins 138. The roller bar allows the weight retaining assembly to be easily moved from one measurement point to another. (The weight retaining assembly is shown in detail in FIG. 8.)

Figure 5:
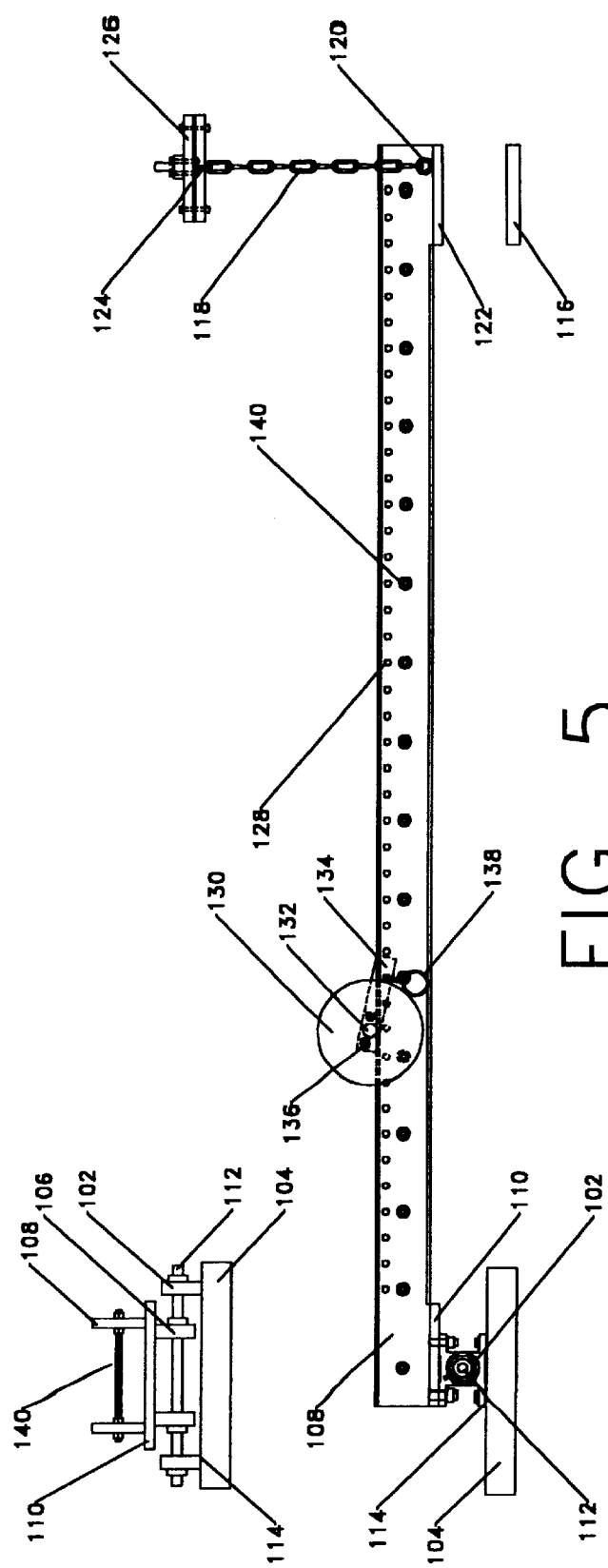
FIG. 5 depicts the side and end views of the modified I-beam version of the present invention with the weight bearing assembly and barbell weights resting on the lever arm. The handle plate assembly and adjustable chain linking system which attaches said assembly to the lever are are shown at the proximal end of the device.
Figure 6:
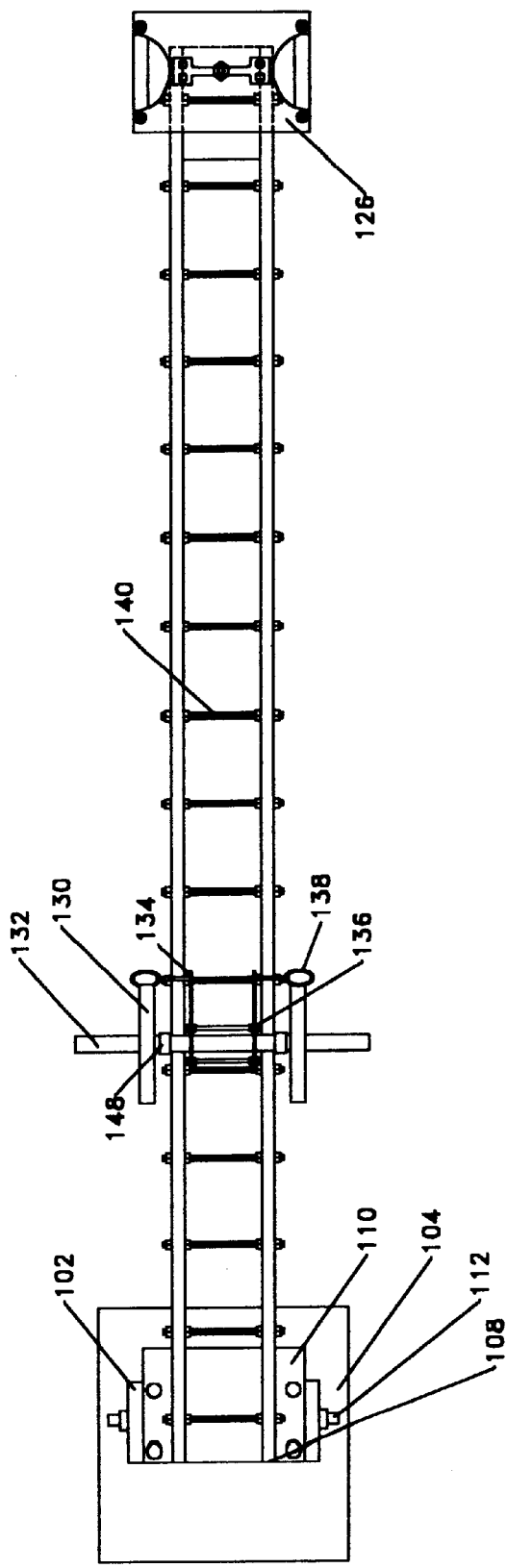
FIG. 6 shows the top view of the modified I-beam version of the present invention with the weight retaining assembly and barbell weights resting on the lever arm.

Referring to FIG. 5 and FIG. 6 which depict a modified I-beam construction, primary bearing boxes 102 are mounted to a base 104. Secondary bearing boxes 106 are affixed at the distal end of a lever arm 108 at the foot plate 110. Said primary and secondary bearing boxes support a rod 112 in a horizontal position. Shims 114 are placed between said primary bearing boxes and said base to provide clearance between the base and the secondary bearing boxes. This arrangement allows said lever arm to pivot in an arc on said rod. The proximal end of the device rests on a floor plate prior 116 to any lifting activity and serves to protect the floor from damage.

One end of an adjustable chain linking system 118 is connected to an eye hook 120 which is affixed to the head plate 122 positioned at the proximal end of the lever arm. The other end of the adjustable chain linking system is attached to and eye hook 124 in the center of the handle plate 126. (The handle plate and adjustable chain linking system are shown in detail in FIG. 7.) The adjustable chain linking system allows the height of said handle plate to be adjusted to the anthropomorphic requirements of the test subject. The use of the eye hooks and adjustable links also allows yawing, pitching and rolling movements of the handle plate to occur during a lift, as might occur during any isoinertial lifting activity in the "real world." In the drawing, the adjustable chain linking system is taut between said foot plate and said handle plate, as would occur during a lifting activity when the device is in use.

Holes 128 in the lever arm are measurement points at which the weight retaining assembly and barbell weights 130 can be secured. Said weight retaining assembly comprises a roller bar 132, straps 134, weight retaining assembly stiffeners 136 (comprising a length of all-thread and four hex nuts) and lynch pins 138. Said roller bar allows the weight retaining assembly to be easily moved from one measurement point to another along the length of the lever arm.(The weight retaining assembly is shown in detail in FIG. 8.)

The sides of this modified I-beam lever arm are maintained in rigid orientation to one another by the use of modified I-beam stiffeners 140 stiffeners (comprising a length of all thread bolts and four hex nuts). Shaft collars 148 maintain the roller bar at a 90 degree orientation to the lever arm, facilitating smooth movement of the weight retaining assembly along the length of the lever arm.

In FIG. 7, a handle 142 for performing unilateral lifts is affixed to the superior surface of the handle plate. Arcs 144 cut into the widths of the handle plate allow a test subject to grasp a handle 146 on each side of the handle plate to perform bilateral lifts.

FIG. 8 illustrates side and top views of the weight retaining assembly. Lynch pins 138 are inserted through holes in the straps 134 and through the holes in the lever arm to secure the weight retaining assembly at a measurement point prior to an attempted lift. Said straps are held in a rigid orientation to one another by use of the stiffeners 136. The stiffeners comprise a length of all-thread and four hex nuts. Barbell weights 130 are placed on a roller bar 132. The roller bar and the rigid orientation of the straps allow the weight retaining assembly to be easily moved from one measurement point to another on the lever arm.

SUMMARY

In accordance with the present invention a lifting capacity assessment device comprises a solid lever arm or modified I-beam lever arm with measurement points located along the length of said lever arm, a fulcrum consisting of a steel bar supported by bearing boxes mounted on the distal end of the device and bearing boxes mounted on a base with said base resting on or secured to a surface, a weight retaining assembly capable of being secured at said measurement points, weight which can be mounted on said weight retaining assembly, a handle appropriate for performing bilateral and unilateral lifts and an adjustable chain linking system connecting said handle plate and the proximal end of the lever arm.

BASIC OPERATION

The manner of using the lever arm lifting assessment device requires adjusting the height of the handle plate by changing the number of adjustable links between the lever arm and the bottom of the handle. The distance of the handle plate from the floor will be determined by the clinician. Consideration should be given to the subject's anthropomorphic characteristics and the demands of the subject's job and be in accordance with clinic policy. The weight retaining assembly is secured at any position on the lever arm determined appropriate by the clinician. Barbell weights are then affixed to the weight retaining assembly in an amount determined appropriate by the clinician. At the clinician's option, more than one weight retaining member can be applied to the lever arm during the protocol.

After the length of the adjustable chain linking system has been set, the clinician lifts the handle, making the adjustable link system taut. The test subject is instructed to assume a position to raise the handle of the invention in a lifting movement. The test subject grasps the handle with one or both hands and lifts the workload. The workload is adjusted by moving the weight bearing assembly closer to, or further from, the fulcrum at the distal end of the device. Additional modifications in the workload can be made by adding weight to, or removing weight from, the roller bar on the weight bearing assembly. At the clinician's option, a second weight bearing assembly and weights can be secured at a measurement point on the lever arm. Testing can be terminated at the clinician's discretion, or when the subject indicates that a maximum lifting capacity has been attained.

An analysis of the consistency of effort offered by the test subject can be accomplished by conducting multiple tests, placing the weight retaining assembly or assemblies at a plurality of locations and increasing or reducing the amount of weight affixed to the weight retaining assembly or assemblies. Results of the repeated trials can then be compared by the clinician.

Another method of analyzing consistency of effort could involve comparisons between performances on each of the two ramifications seen in the drawings. Additional analysis for consistency of effort could involve making comparisons of a test subject's performance on the present invention with comparable lifts using other testing equipment. Comparable lifts which do not use this invention could involve either marked or unmarked weights. These performances could subsequently be compared to a capacities measured on the present device. Actual workloads lifted by a subject can be determined by referring to a table supplied by the manufacturer.

CONCLUSIONS, RAMIFICATIONS AND SCOPE

Accordingly, the reader will see that the lever arm lifting capacity testing device can be used to analyze consistency of effort during a test of a subject's bilateral and unilateral lifting abilities. Furthermore, the lever arm lifting assessment device has additional advantages in that:

a) the high number of permutations with regard to possible workloads that can be applied make it difficult for a test subject to guess the amount of weight being lifted. This feature will enhance the ability of a clinician to objectively identify inconsistencies in performance by conducting multiple trials and subsequently analyzing the differences in physical performance between the trials;

c) the high number of permutations with regard to possible workloads that can be applied will make it possible for the same subject to be re-tested on the device without the previous exposure to the invention affecting the objectivity of the assessment.

d) the cost of this invention will be substantially less than inventions which utilize electronic means to measure or apply workloads.

e) there is no need to periodically re-calibrate the device because any given workload at any given position on the lever arm will always offer the same resistance because of basic and unchanging laws of physics.

g) the device takes up a minimal amount of space and can be easily stored.

h) the device is easy to use and will take a minimal amount of training time for a clinician to become proficient in its use;

i) the device has few moving parts and will be inexpensive to maintain.

j) the device measures isoinertial lifting capacity, which has relevance for the actual workplace.

Although the description above contains many specificities, these should not be construed as limiting the scope of the invention but as merely providing illustrations of some of the presently preferred embodiments of this invention. For example, the lever arm could be made of wood, metal, composite, or synthetic material or any combination of materials. The fulcrum could be located at any point in the distal one-half of the lever arm. The fulcrum could be made of a material other than steel. A hinge could replace the present fulcrum. In another embodiment, the lever arm could include a counterweight system. The lever arm could be hollow or made of other shapes including cylindrical, rectangular, triangular, octagonal, I-beam or T-beam. The length of the lever arm could be made adjustable. The lever arm could be made of various lengths. Multiple lever arms could be incorporated into the device. The adjustable link system could also be made of wire, cable, chain, rope or strap, either with or without provision to adjust the distance between the handle plate and the lever arm. The moveable weight retaining assembly could be replaced by a sled on which the weights are stacked and subsequently secured at various points along the lever arm. In another version, hooks or clamps statically affixed to the lever arm could serve as measurement points at which a weight could be secured. Weight could be stacked on the top surface of the lever arm, or secured on the sides or bottom surface of the lever arm. Stiffeners used for the weight retaining assembly and the modified I-beam lever arm could be of larger or smaller dimensions than those depicted in the drawings and could be placed at intervals different from those which are illustrated. The shaft collars used in the modified I-beam ramification could be eliminated. The handle made for use during unilateral lifts could be eliminated. In another ramification, a single weight retaining assembly could be employed. Thus, the scope of the invention should be determined by the appended claims and their legal equivalents, rather than by the examples given.

REFERENCES

Agre J, Magness J, Hull S, Wright K, Baxter T, Patterson R, et. al.: Strength Testing with a Portable Dynamometer; Reliability for Upper and Lower Extremities. Archives of Physical Medicine and Research, 68:454–458, 1988.

Mital A, Karwowski W, Mazoua A, Orsarh E: Prediction of Maximum Acceptable Weight of Lift in the Horizontal and Vertical Planes Using Simulated Job Dynamic Strengths, American Industrial Hygiene Association Journal, 47(5):288–292, 288–291, 1986.

Battie M, Bigos S, Fisher L, Hansson T, Jones M, Wortley M: Isometric Lifting Strength as a Predictor of Low Back Pain, Spine, 14:851–856, 1989.

Beaton D, O'Driscoll S, Richards R: Grip Strength Testing Using the BTE Work Simulator and the Jamar Dynamometer: A Comparative Study. Journal of Hand Surgery, 20A(2):293–298, March, 1995

Blankenship K: *Industrial Rehabilitation: A Seminar Syllabus*, American Therapeutics, Inc., 1990.

Bohannon R: Differentiation of Maximal from Submaximal Static Elbow Flexor Efforts by Measurement Variability. American Journal of Physical Medicine, 66(5):213–217, 1987

Fairfax A, Balnave R, Adams R: Variability of Grip Strength During Isometric Contraction. Ergonomics, 38(9):1819–1830, 1995

Fromoyer J, Cats-Baril W. Predictors of Low Back Pain Disability. Clinical Orthopeadics, 221:89–98.

Fromoyer J, Pope M, Clements J, Wilder D, MacPherson B, Ashikaga T: Risk Factors in Low-Back Pain: An Epidemiological Study, Journal of Bone and Joint Surgery, 8(8): 14–24, 1991.

Harber P, SooKoo K: Static Ergonomic Strength Testing in Evaluation of Occupational Back Pain, Journal of Occupational Medicine, 26:877–884, 1984

Hirsch G, Beach G, Cooke C, Menard M, Lock S: Relationship Between Performance on Lumbar Dynamometry and Waddell Score in a Population with Low Back Pain. Spine, 16(9):1039–1043, 1991

Isernhagen S, *Comprehensive Guide to Work Injury Management*, Aspen Publishing, Gaithersburg, Md., 1995.

Klenerman L, Slade P, Stanley M, Pennie B, Reilly J, Atchison L, Troup J, Rose M: The Prediction of Chronicity in Patients With an Acute Attack of Low Back Pain in General Practice Setting. Spine, 20(4):478–484, 1995.

Matheson L. How Do You Know He Tried His Best? Industrial Rehabilitation Quarterly, 1:82–82, 1988.

Matheson L. *Symptom Magnification Syndrome*, Presented in a symposium by Roy Matheson and Associates, 1991.

Matheson L. *Work Capacity Evaluation: Systematic Approach to Industrial Rehabilitation*. Employment and Rehabilitation Institute of California, Anaheim, Calif., 1986.

Mechanic D: The Concept of Illness Behavior. Journal of Chronic Disorders, 15: 182–184, 1967.

Menard M, Cooke C, Locke S, Beach C Butler T: Pattern of Performance in Low Back Pain During a Comprehensive Motor Performance Evaluation. Spine, 19(12):1359–1366, 1994.

Robinson M, Macmillan M, O'Connor P, Fuller a, Cassisi J. Reproducibility of Maximal Versus Submaximal Efforts in and Isometric Lumbar Extension Task. Journal of Spinal Disorders, 4:444–448, 1991.

Simonsen, J: Coefficient of Variation as a Measure of Sincere Effort, Archives of Physical Medicine and Rehabilitation, 76:516–520, 1995.

Snook S: The Costs of Back Pain in Industry, Spine, 2:1–5, 1987.

Spengler D, Bigos S. Martin N, et. al.: Back Injuries in Industry, Spine, 11:241–245, 1986.

Spengler D, Szpalski M: Newer Assessment Approaches for the Patient with Low Back Pain. Contemporary Orthopaedics, 21(4): October 1990

Waddell G: A New Clinical Model for the Treatment of Low-Back Pain, Spine, 12:632–644, 1987.

Waddell G, Main C, Morris E, Paola M, Gray I: Chronic Low-Back Pain, Psychologic Distress, and Illness Behavior. Spine, 9:209–213, 1984.

Waddell G, McCulloch J, Kummel E, Venner R: Nonorganic Physical Signs in Low-Back Pain. Spine, 5(2), 1980.

What is claimed is:

1. A lifting capacity testing device for cross reference test results in a functional capacity evaluation comprising:

a lever arm having a distal end, a proximal end, and a plurality of measuring points along the length of said lever arm, a fulcrum located on the said lever arm and comprising a rod supported in a horizontal position by a plurality of bearing boxes affixed to the distal end of said lever arm and a plurality of bearing boxes affixed to a base which is secure to, or rests on a surface, a handle plate connected to the proximal end of said lever arm with said handle suitable for performing a lifting activity, a weight retaining assembly capable of securing a workload a any measuring points, and a weight which is affixed to said retaining assembly, said workload is applied to said lever arm and a test subject exert a lifting force on the handle plate, causing the distal end of the lever arm to pivot on the fulcrum, thus raising the handle plate, the proximal end of the lever arm, the weight retaining assembly and the weight thereto enabling an evaluator to assess validity of effort in a multiple trial lifting assessment.

* * * * *